United States Patent [19]
Homma et al.

[11] Patent Number: 5,123,950
[45] Date of Patent: Jun. 23, 1992

[54] COATED AGRICULTURAL CHEMICALS

[75] Inventors: Yasuo Homma, Sakado; Yutaka Arimoto, Niiza, both of Japan

[73] Assignee: Rikagaku Kenkyusho, Wako, Japan

[21] Appl. No.: 504,009

[22] Filed: Apr. 4, 1990

[51] Int. Cl.[5] .............................................. C05G 3/00
[52] U.S. Cl. .......................................... 71/11; 71/27; 71/64.07; 71/64.08; 71/64.13; 71/3
[58] Field of Search ............... 71/1, 11, 27, 28, 64.07, 71/64.08, 64.13

[56] References Cited

U.S. PATENT DOCUMENTS

| | | | |
|---|---|---|---|
| 3,706,545 | 12/1972 | Gray et al. | 71/27 X |
| 3,799,755 | 3/1974 | Rack | 71/24 |
| 4,394,149 | 7/1983 | Szoka, Jr. et al. | 71/27 X |
| 4,599,233 | 2/1986 | Misato et al. | 424/717 |

FOREIGN PATENT DOCUMENTS 2075344 11/1981 United Kingdom .
2213378 8/1989 United Kingdom .

Primary Examiner—Ferris Lander
Attorney, Agent, or Firm—Oblon, Spivak, McClelland, Maier & Neustadt

[57] ABSTRACT

A coated agricultural chemical comprises a powdery effective component of an agricultural chemical coated with at least one member selected from the group consisting of esters of aliphatic acids and aliphatic polyols and phospholipids in an amount of 0.1 to 3 parts by weight per 100 parts by weight of the effective component. The agricultural chemicals exhibit high efficiency even at a concentration lower than that conventionally used and low phytotoxicity to plants.

9 Claims, 6 Drawing Sheets

5,123,950

COATED AGRICULTURAL CHEMICALS

BACKGROUND OF THE INVENTION

1. Field of the Invention

The present invention relates to coated agricultural chemicals or formulations which can exhibit sufficiently high efficiency even at a concentration lower than that of conventionally used.

2. Description of the Prior Art

Hitherto, there have widely been used such heavy metal compounds as cupreous agents, mercurials and arsenicals; organochlorine agricultural chemicals and organophosphorus agricultural chemicals as formulations of agricultural chemicals. However, all of these agricultural chemicals are not only harmful to human body and animals but also contaminate the soil which leads to environmental pollution developed into a severe social problem accompanied by the use of effective amount thereof.

Under such circumstances, Japanese Patent Publication for Opposition Purpose (hereunder referred to as "J. P. KOKOKU") No. 57-48525 teaches that a fungicide mainly composed of an ester of an aliphatic polyol and an aliphatiac acid and sodium hydrogen carbonate shows a prevention effect on various blight of plants and those observed during storing fruits and is highly safe with respect to human body, animals and plants.

However, the agricultural chemicals prepared according to such a method must be used in a high concentration in order to achieve a desired efficiency when they are used in an amount comparable to that of the conventional ones and on the contrary, if the concentration thereof is limited to a low level, a desired efficiency is attained only when they are used in a large amount.

To eliminate such disadvantages, the inventors of this invention developed a formulation of agricultrual chemicals (see Japanese Patent Unexamined Published Application (hereunder referred to as "J. P. KOKAI") No. 63-233902). However, such a formulation is not still satisfied since it provides a desired effect only when the concentration of the effective component is relatively high, and when the state of blight occurrence is severe, its effect becomes low.

SUMMARY OF THE INVENTION

Accordingly, an object of the present invention is to provide coated agricultural chemicals or formulations which exhibit high efficiency even at a low concentration.

The aforementioned object of the present invention can be achieved by providing a coated agricultural chemical which comprises a powdery effective component of an agricultural chemical coated with at least one member selected from the group consisting of aliphatic acid esters of aliphataic polyols and phospholipids in an amount of 0.1 to 3 parts by weight per 100 parts by weight of the effective component.

BRIEF EXPLANATION OF THE DRAWINGS

The present invention will hereunder be explained in more detail with reference to the accompanied drawings, wherein.

DETAILED EXPLANATION OF THE INVENTION

Figure 1:
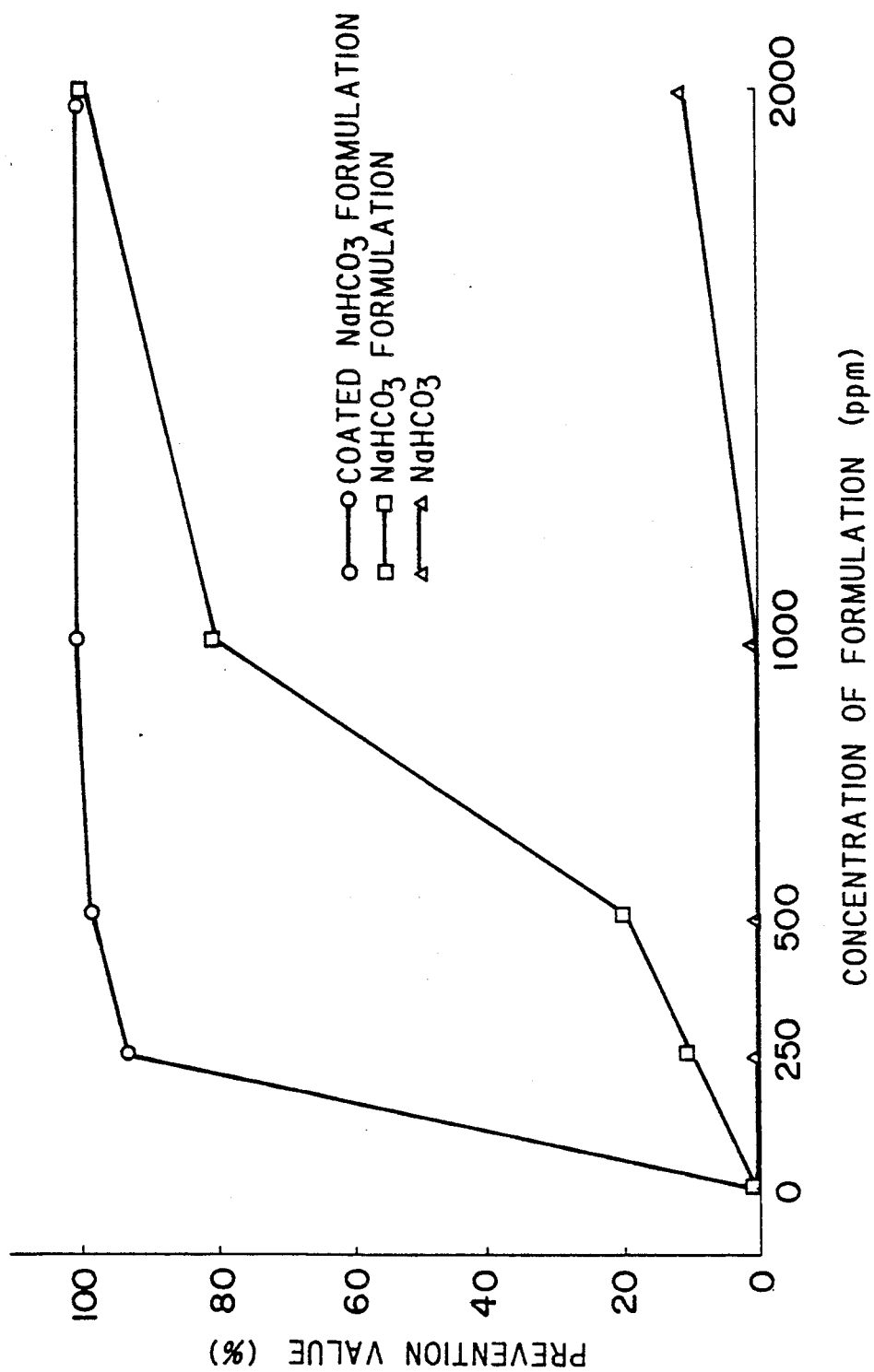
FIG. 1 shows the prevention value of various agricultural formulations for black spot disease of oranges, plotted against the concentration of the formulation.

The coated agricultural chemicals or formulations (hereunder simply referred to as "agricultural chemicals" or "agricultural formulations") of the present invention can be prepared by dissolving 0.1 to 3 parts of at least one member selected from the group consisting of aliphatic acid esters of aliphatic polyols and phospholipids in a proper solvent such as acetone, adding 100 parts of a powdery effective component of an agricultural chemical to the solution, mixing them while stirring and then distilling off the solvent.

As the aliphatic polyol moieties from which the aliphatic acid esters of aliphatic polyols used herein are produced, there may be employed saturated and unsaturated aliphatic polyols having 3 to 6 carbon atoms and preferred are glycerin, propylene glycol, sorbitol and sorbitan.

On the other hand, examples of the aliphataic acid moieties of the aliphatic acid esters of polyols herein used are individual aliphatic acids such as saturated aliphatic acids, for instance, caprylic acid, capric acid, lauric acid, myristic acid, palmitic acid, stearic acid, arachic acid and behenic acid; or unsaturated aliphatic acids, for instance, oleic acid, linolic acid, linolenic acid and ricinoleic acid; mixed aliphatic acids such as those naturally derived from animals or plants, for instance, tallow, cottonseed oil, rapeseed oil and hardened oil.

Examples of the aliphatic acid esters of the aliphatic polyols as one of main components of the coated agricultural chemicals of the invention are mono-, di- or triesters prepared by esterifying or ester-interchanging the foregoing aliphataic polyols and aliphatic acids, in particular sorbitan monolaurate, sorbitan monostearate, glycerin monooleate, glycerin monooctoate, glycerin mono-soyabean oil fatty acid ester, glycerin mono-cottonseed oil fatty acid ester, triglycerin monooleate, glycerin monopalmitate and polyglycerin fatty acid esters are preferably used.

Moreover, examples of the phospholipids used herein are phytolecithin derived from plant's oils and egg yolk lecithin; and phosphatidylcholine, phosphatidylethanolamine and phosphatidylinositol separated therefrom.

The effective components of the agricultural chemicals of the present invention may be any agricultural chemicals which are in the form of solid powder at ordinary temperature and examples thereof include various germicides, insecticides and herbicides for agricultural and horticultural use. The effective components may be water-insoluble ones, but preferably water-soluble ones.

Specific examples of the effective components of the agricultural chemicals include ordinary agricultural chemicals such as copper 8-oxyquinoline, basic copper sulfate, copper sulfate (anhydrous), copper sulfate pentahydrate, basic copper chloride, copper (II) chloride, basic copper carbonate, methyl 1-(butylcarbamoyl)-2-benzimidazolecarbamate, antibiotic-polyoxine complex, o,o-diethyl-s-benzylthiophosphate, 2-sec-butylphenyl-N-methylcarbamate and o,o-dimethyl-2, 2, 2-trichloro-1-hydroxyethylphosphate; and sodium hydrogen carbonate, sodium carbonate, potassium hydrogen carbonate, potassium carbonate, calcium carbonate, ammonium carbonate, ammonium hydrogen carbonate, sodium chloride, potassium chloride, disodium hydrogen phosphate, sodium dihydrogen phosphate, dipotassium hydrogen phosphate and potassium dihydrogen phosphate which are highly safe against animals and plants.

In the coated agricultural chemicals, the amount of the coating agent, i.e., aliphatic acid esters of aliphatic polyols and/or phospholipids ranges from 0.1 to 3 parts per 100 parts of the effective component. This is because if the amount is outside the foregoing range, the following problems arises when the agricultural chemicals are used by diluting these with water. In other words, if the amount of the coating agent is less than 0.1 part, the agricultural chemicals cannot effectively be emulsified. On the other hand, if it is more than 3 parts, the agricultural chemicals cannot frequently be emulsified effectively since the ester portions are separated and hence the coating film cannot be maintained. However, such an emulsion can be obtained depending on the kinds of the effective component of the argricultural chemicals.

The particle size of the effective components of the agricultural chemicals is preferably adjusted so that it passes through a sieve of 100 mesh, more preferably 200 to 400 mesh, since it is difficult to maintain the coating film if the particle size is too large.

The coated agricultural chemicals of the present invention may further comprise auxiliary agents commonly incorporated in compositions of agricultural chemicals such as surfactants, which do not destroy the emulsion, for instance, spreading agents, wetting and spreading agents and anchorages according to need and then are converted to agricultural formulations.

The concentration thereof to be sprayed varies dependent upon the kinds of the effective components and is not limited to a specific range, but preferred concentration threof ranges from about 1 to 500 ppm.

The agricultural formulations of the present invention will hereunder be explained in more specifically with reference to Examples, but the invention is not restricted to these specific Examples. Moreover, the effects practically attained by the present invention will also be discussed below in comparison with Comparative Examples.

EXAMPLE 1

Glycerin monooleate (2 g) was dissolved in 100 cc of acetone. Then 80 g of fine powder of sodium hydrogen carbonate, 90% of which passed through a sieve of 100 mesh, was aded to the solution, followed by sufficiently stirring the mixture and completely distilling off the solvent utilizing a rotary evaporator to obtain powdery product. To the powdery product there was added 10 g of powdery sodium casein and the ingredients were admixed to form a powdery hydrated formulation having good flowability.

EXAMPLE 2

Polyglycerin fatty acid ester (1 g) was dissolved in 100 cc of acetone. Then 80 g of fine powder of sodium hydrogen carbonate, 90% of which passed through a sieve of 100 mesh, was added to the solution, followed by sufficiently stirring the mixture and completely distilling off the solvent utilizing a rotary evaporator to obtain a wettable powder.

EXAMPLE 3

Glycerin monooleate (0.5 g) and glycerin monooctoate (0.3 g) were dissolved in 100 cc of acetone. Then 80 g of fine powder of sodium carbonate, 90% of which passed through a sieve of 100 mesh, was added to the solution, followed by sufficiently stirring the mixture and completely distilling off the solvent utilizing a rotary evaporator to obtain powdery product. To the powdery product there was added 10 g of powdery sodium casein and these ingredients were admixed to form a wettable powder having good flowability.

EXAMPLE 4

Glycerin monooleate (0.5 g) and glycerin monooctoate (0.3 g) were dissolved in 100 cc of acetone. Then 80 g of fine powder of potassium carbonate, 90% of which passed through a sieve of 100 mesh, was added to the solution, followed by sufficiently stirring the mixture and completely distilling off the solvent utilizing a rotary evaporator to obtain powdery product. To the powdery product there was added 10 g of powdery sodium casein and these ingredients were admixed to form a wettable powder having good flowability.

EXAMPLE 5

Glycerin monooleate (0.5 g) and glycerin monooctoate (0.3 g) were dissolved in 100 cc of acetone. Then 80 g of fine powder of ammonium carbonate, 90% of which passed through a sieve of 100 mesh, was added to the solution, followed by sufficiently stirring the mixture and completely distilling off the solvent utilizing a rotary evaporator to obtain powder. To the powder there was added 10 g of powdery sodium casein and the mixture was admixed to form a wettable powder having good flowability.

EXAMPLE 6

Glycerin monooleate (0.5 g) and glycerin monooctoate (0.3 g) were dissolved in 100 cc of acetone. Then 80 g of fine powder of ammonium hydrogen carbonate, 90% of which passed through a sieve of 100 mesh, was added to the solution, followed by sufficently stirring the mixture and completely distilling off the solvent utilizing a rotary evaporator to obtain powder. To the powder there was added 10 g of powdery sodium casein and the mixture was admixed to form a wettable powder having good flowability.

EXAMPLE 7

Glycerin monooleate (0.5 g) and glycerin monooctoate (0.3 g) were dissolved in 100 cc of acetone. Then 80 g of fine powder of potassium hydrogen carbonate, 90% of which passed through a sieve of 100 mesh, was added to the solution, followed by sufficiently stirring the mixture and completely distilling off the solvent utilizing a rotary evaporator to obtain powder. To the powder there was added 10 g of powdery sodium casein and the mixture was admixed to form a wettable powder having good flowability.

EXAMPLE 8

Glycerin monooleate (2.5 g) and glycerin monooctoate (1.5 g) were dissolved in 100 cc of acetone. Then 80 g of fine powder of potassium chlorine, 90% of which passed through a sieve of 100 mesh, was added to the solution, followed by sufficiently stirring the mixture and completely distilling off the solvent utilizing a rotary evaporator to obtain powder. To the powder there was added 10 g of powdery sodium casein and the mixture was admixed to form a wettable powder having good flowability.

EXAMPLE 9

Glycerin monooleate (0.5 g) and glycerin monooctoate (0.3 g) were dissolved in 100 cc of acetone. Then 80 g of fine powder of sodium chloride, 90% of which passed through a sieve of 100 mesh, was added to the solution, followed by sufficiently stirring the mixture and completely distilling off the solvent utilizing a rotary evaporator to obtain powder. To the powder there was added 10 g of powdery sodium casein and the mixture was admixed to form a wettable powder having good flowability.

EXAMPLE 10

Glycerin monooctoate (0.8 g) was dissolved in 100 cc of acetone. To the solution 80 g of Benlate (methyl-1-(butylcarbamoyl)-2-benzimidazolecarbamate) was added, followed by sufficiently stirring the mixture, then completely distilling off the solvent to obtain a wettable powder.

EXAMPLE 11

Glycerin monooleate (0.5 g) and glycerin monooctoate (0.2 g) were dissolved in 100 cc of acetone. To the solution there were added 80 g of Polyoxin AL (antibiotic-polyoxin complex) and lactose, followed by sufficiently stirring the mixture and distilling off the solvent therefrom to obtain powdery product. Then 5 g of white carbon was added to the powder to form a wettable powder having good flowability.

EXAMPLE 12

Glycerin monooleate (0.5 g) and glycerin monooctoate (0.2 g) were dissolved in 100 cc of acetone. To the solution there were added 80 g of Kitazin P (o,o-diethyl-s-benzylthiophosphate) and lactose, followed by sufficiently stirring the mixture and distilling off the solvent therefrom to obtain powdery product. Then 5 g of white carbon was added to the powder to form a wettable powder having good flowability.

EXAMPLE 13

Polyglycerin fatty acid ester (0.5 g) and glycerin monooctoate (0.2 g) were dissolved in 100 cc of acetone. To the solution there were added 80 g of Bassa (BPMC: 2-sec-butylphenyl-N-methylcarbamate) and lactose, followed by sufficiently stirring the mixture and distilling off the solvent therefrom to obtain powdery product. Then 5 g of white carbon was added to the powder to form a wettable powder having good flowability.

EXAMPLE 14

Polyglycerin fatty acid ester (0.5 g) and glycerin monooctoate (0.2 g) were dissolved in 100 cc of acetone. To the solution there were added 80 g of DEP (o,o-dimethyl-2,2,2-trichloro-1-hydroxyethylphosphate) and lactose, followed by sufficiently stirring the mixture and distilling off the solvent therefrom to obtain powdery product. Then 5 g of white carbon was added tot he powder to form a wettable powder having good flowability.

EXAMPLE 15

Polyglycerin fatty acid ester (0.5 g), glycerin monooctoate (0.2 g) and glycerin monooleate (0.1 g) were dissolved in 100 cc of acetone. To the solution there were added 80 g of Bialaphos (see Journal of Antibiotaics (J. A.), 1983, Vol. 36, No. 8, pp. 1040-1044) and lactose, followed by sufficiently stirring the mixture and distilling off the solvent therefrom to obtain powdery product. Then 5 g of white carbon was added to the powder to form a wettable powder having good flowability.

EXAMPLE 16

Glycerin monooleate (2.5 g) and glycerin monooctoate (1.5 g) were dissolved in 100 cc of acetone. Then 80 g of fine powder of copper sulfate ($5H_2O$) was added to the solution, followed by sufficiently stirring the mixture and completely distilling off the solvent utilizing a rotary evaporator to obtain powder. To the powder there was added 10 g of powdery sodium casein and the mixture was admixed to form a wettable powder having good flowability.

EXAMPLE 17

Glycerin monooleate (0.5 g) and glycerin monooctoate (0.3 g) were dissolved in 100 cc of acetone. Then 80 g of fine powder of anhydrous copper sulfate was added to the solution, followed by sufficiently stirring the mixture and completely distilling off the solvent utilizing a rotary evaporator to obtain powder. To the powder there was added 10 g of powdery sodium casein and the mixture was admixed to form a wettable powder having good flowability.

EXAMPLE 18

Glycerin monooctoate (0.8 g) was dissolved in 100 cc of acetone. To the solution 80 g of fine powder of copper 8-oxyquinoline was added, followed by sufficiently stirring the mixture, then completely distilling off the solvent to obtain a wettable powder.

EXAMPLE 19

Glycerin monooleate (0.5 g) and glycerin monooctoate (0.2 g) were dissolved in 100 cc of acetone. To the solution there were added 80 g of basic copper chloride and lactose, followed by sufficiently stirring the mixture and distilling off the solvent therefrom to obtain powdery product. Then 5 g of white carbon was added to the powder to form a wettable powder having good flowability.

EXAMPLE 20

Two parts by weight of the formulation of Example 1 was mixed with one part by weight of the formulation of Example 17.

EXAMPLE 21

One part by weight of the formulation of Example 7 was mixed with one part by weight of the formulation of Example 18.

EXAMPLE 22

One part by weight of the formulation of Example 1 was mixed with one part by weight of the formulation of Example 18.

TEST EXAMPLES 1 to 13

The effects achieved by aqueous solutions of various kinds of coated carbonates and hydrogen carbonates of the present invention were estimated and were compared with those achieved by aqueous solutions of the aforesaid agricultural formulations (J. P. KOKAI No. 63-233902) and conventional agricultural chemicals.

The comparison between these results was performed by preparing solutions of each agricultural chemical having concentrations of 500 and 200 ppm, determining prevention values (%) at 4 and 6 days after the application or spraying and simultaneously estimating phytotoxicity of the agricultural chemicals used. The results observed are listed in Table I.

In Table I, the prevention values of the solutions having a concentration of 200 ppm is given in brackets. On the other hand, the phytotoxicity of each agricultural chemical was almost the same regardless of te concentration of the solutions (200 and 500 ppm) and thus the results were summarized and listed therein.

For the purpose of comparison, the effect observed when a solution free of effective components was used is also listed in Table I as a control.

It is found, from the results summarized in Table I, that the coated agricultural formulations of the present invention are effective and show extremely high prevention values even when they were used in a low concentration such as 200 and 500 ppm compared with the results observed on the conventional agricultural chemicals and agricultural formulations.

TABLE I

The prevention effect of various coated carbonates, hydrogen carbonates on mildew of cucumber.

| Test No. | Formulation tested | Concn. (ppm) | Prevention Value (%) 4 days | Prevention Value (%) 6 days | Phytotoxicity |
|---|---|---|---|---|---|
| Test 1 (Ex. 1) | coated $NaHCO_3$ formulation | 550 (200) | 94(90) | 90(85) | none |
| | $NaHCO_3$ formulation | 500 (200) | 51(21) | 47(18) | none |
| | $NaHCO_3$ | 500 (200) | 18(0) | 10(0) | none |
| Test 2 (Ex. 3) | coated $Na_2CO_3$ formulation | 500 (200) | 100(89) | 100(84) | none |
| | $Na_2CO_3$ formulation | 500 (200) | 47(17) | 42(13) | none |
| | $Na_2CO_3$ | 500 (200) | 10(1) | 5(0) | none |
| Test 3 (Ex. 4) | coated $K_2CO_3$ formulation | 500 (200) | 100(91) | 98(88) | none |
| | $K_2CO_3$ formulation | 500 (200) | 48(11) | 46(11) | none |
| | $K_2CO_3$ | 500 (200) | 16(0) | 11(0) | none |
| Test 4 | coated $CaCO_3$ formulation | 500 (200) | 100(87) | 100(81) | none |
| | $CaCO_3$ formulation | 500 (200) | 41(10) | 32(7) | none |
| | $CaCO_3$ | 500 (200) | 18(0) | 10(0) | none |
| Test 5 (Ex. 5) | coated $(NH_4)_2CO_3$ formulation | 500 (200) | 100(86) | 100(82) | none |
| | $(NH_4)_2CO_3$ formulation | 500 (200) | 38(5) | 29(0) | none |
| | $(NH_4)_2CO_3$ | 500 (200) | 7(0) | 3(0) | none |
| Test 6 (Ex. 6) | coated $(NH_4)HCO_3$ formulation | 500 (200) | 97(83) | 95(80) | none |
| | $(NH_4)HCO_3$ formulation | 500 (200) | 35(8) | 30(0) | none |
| | $(NH_4)HCO_3$ | 500 (200) | 8(0) | 5(0) | none |
| Test 7 (Ex. 9) | coated NaCl formulation | 500 (200) | 97(90) | 92(85) | none |
| | NaCl formulation | 500 (200) | 50(21) | 44(21) | none |
| | NaCl | 500 (200) | 20(0) | 15(0) | none |
| Test 8 (Ex. 8) | coated KCl formulation | 500 (200) | 100(94) | 98(91) | none |
| | KCl formulation | 500 (200) | 47(0) | 45(0) | none |
| | KCl | 500 (200) | 20(0) | 10(0) | none |
| Test 9 (Ex. 7) | coated $KHCO_3$ formulation | 500 (200) | 100(98) | 100(92) | none |
| | $KHCO_3$ formulation | 500 (200) | 42(15) | 38(13) | none |
| | $KHCO_3$ | 500 (200) | 20(0) | 20(0) | none |
| Test 10 | coated $Na_2HPO_4$ formulation | 500 (200) | 98(90) | 91(81) | none |
| | $Na_2HPO_4$ formulation | 500 (200) | 32(22) | 30(22) | none |
| | $Na_2HPO_4$ | 500 (200) | 20(10) | 20(5) | none |
| Test 11 | coated $NaH_2PO_4$ formulation | 500 (200) | 100(100) | 100(93) | none |
| | $NaH_2PO_4$ formulation | 500 (200) | 40(23) | 30(25) | none |
| | $NaH_2PO_4$ | 500 (200) | 30(5) | 28(0) | none |
| Test 12 | coated $K_2HPO_4$ formulation | 500 (200) | 98(94) | 93(93) | none |
| | $K_2HPO_4$ formulation | 500 (200) | 28(14) | 25(12) | none |
| | $K_2HPO_4$ | 500 (200) | 25(5) | 20(0) | none |
| Test 13 | coated $KH_2PO_4$ formulation | 500 (200) | 100(90) | 97(89) | none |
| | $KH_2PO_4$ formulation | 500 (200) | 38(11) | 32(11) | none |
| | $KH_2PO_4$ | 500 (200) | 31(3) | 15(1) | none |
| Control | none | | 0(0) | 0(0) | none |

Note: The prevention values given in the brackets correspond to the data obtained when the formulation was used at the concentration given in the brackets.

TEST EXAMPLES 14 to 25

The coated agricultural formulations of the present invention were prepared by using methyl 1-(butylcarbamoyl)-2-benzimidazole-carbamate, antibiotic-polyoxin complex, o,o-diethyl-s-benzylthiophosphate, 2-sec-butylphenyl-N-methylcarbamate, o,o-dimethyl-2,2,2-trichloro-1-hydroxyethylphosphate and Bialaphos. In order to examine the variation in effect with the change in the concentration, the prevention value for grey mildew of cucumber and tomato, the rate of death for *thrips plami* and tabacco cutdown (*Prodenia litura*), and efficiency index for culy dock (*Rumex obtusifolius L.*) were estimated. The prevention value was estimated from the following relation:

$$\text{Prevention Value (\%)} = \left(1 - \frac{\text{Number of Rotten Parts in } T.D.}{\text{Number of Rotten Parts in } N.T.D.}\right) \times 100$$

In addition, the efficiency index was calculated from the following relation:

$$\text{Efficiency Index} = \left(1 - \frac{\text{Survival Rate of Insects in } T.D.}{\text{Survival Rate of Insects in } N.T.D.}\right) \times 100$$

In these relations, T.D. and N.T.D. represent treated domain and nontreated domain respectively.

The results observed are summarized in Table II below.

For grey mildew of cucumber and tomato, the prevention value of the coated methyl 1-(butylcarbamoyl)-2-benzimidazolecarbamate was remarkably enhanced in the concentration range of 10 to 80 ppm as the concentration increases, compared with the aqueous solution of the same agricultural chemical conventionally used.

The prevention values of the coated antibiotic-polyoxin complex for grey mildew of cucumber and tomato were all not less than 90% between 25 and 100 ppm while those of the aqueous solution of the conventional agricultural formulations were all not more than 50%.

In addition, it is found that the coated o,o-diethyl-s-benzylthiophosphate exhibits the prevention values for grey mildew of tomato ranging from 89 to 98% between 60 and 480 ppm while those of the aqueous solution of the non-coated one ranges from 24 to 76%. This clearly indicates that the coated formulation is effective to such a disease. The coated 2-sec-butylphenyl-N-methylcarbamate exhibits the rate of death for thrips palmi ranging from 75 to 96% between 50 and 150 ppm while that of the ordinary aqueous solution of the non-coated one ranges from 5 to 18%.

The coated o,o-dimethyl-2,2,2-trichloro-1-hydroxyethylphosphate exhibits the rate of death for tabacco cutdown ranging from 76 to 100% between 50 and 150 ppm while that of the ordinary aqueous solution of the non-coated one ranges from 0 to 15%. It is also found that the coated so-called Bialaphos increases the efficiency index for culy dock 2 to 3 times larger than that of an aqueous solution of the non-coated one in a concentration range of 60 to 500 ppm.

TABLE II

Prevention Effect of Various Coated Formulations on Various diseases

| Test No. | Formulation Tested | Concn. (ppm) | P.V. for G.M. of cucumber | P.V. for G.M. of tomato |
| --- | --- | --- | --- | --- |
| 14 | Ex. 10 (coated Benlate) | 10 | 91 | 87 |
|  | Ex. 10 (coated Benlate) | 20 | 92 | 92 |
|  | Ex. 10 (coated Benlate) | 40 | 95 | 97 |
|  | Ex. 10 (coated Benlate) | 80 | 96 | 99 |
|  | Benlate | 10 | 21 | 20 |
|  | " | 20 | 33 | 37 |
|  | " | 40 | 57 | 51 |
|  | " | 80 | 71 | 70 |
| 15 | Ex. 11 (coated polyoxin AL) | 25 | 90 | 92 |
|  | Ex. 11 (coated polyoxin AL) | 50 | 95 | 96 |
|  | Ex. 11 (coated polyoxin AL) | 100 | 98 | 99 |
|  | polyoxin AL | 25 | 0 | 0 |
|  | " | 50 | 11 | 8 |
|  | " | 100 | 42 | 25 |
| 16 | Ex. 12 (coated Kitazin-P) | 60 |  | 89 |
|  | Ex. 12 (coated Kitazin-P) | 120 |  | 93 |
|  | Ex. 12 (coated Kitazin-P) | 240 |  | 96 |
|  | Ex. 12 (coated Kitazin-P) | 480 |  | 98 |
|  | Kitazin-P | 60 |  | 24 |
|  | " | 120 |  | 33 |
|  | " | 240 |  | 50 |
|  | " | 480 |  | 76 |

| Test No. | Formulation Tested | Concn. (ppm) | Rate of Death(%) for thrips palmi | Rate of Death(%) for tabacco cutdown | Efficiency Index for culy dock |
| --- | --- | --- | --- | --- | --- |
| 17 | Ex. 13 (coated Bassa) | 50 | 75 |  |  |
|  | Ex. 13 (coated Bassa) | 100 | 89 |  |  |
|  | Ex. 13 (coated Bassa) | 150 | 96 |  |  |
|  | Bassa (BPMC) | 50 | 5 |  |  |
|  | Bassa (BPMC) | 100 | 10 |  |  |
|  | Bassa (BPMC) | 150 | 18 |  |  |
| 18 | Ex. 14 (coated DEP) | 50 |  | 76 |  |
|  | Ex. 14 (coated DEP) | 100 |  | 92 |  |
|  | Ex. 14 (coated DEP) | 150 |  | 100 |  |
|  | Ex. 14 (coated DEP) | 200 |  | 100 |  |
|  | DEP | 50 |  | 0 |  |
|  | " | 100 |  | 0 |  |
|  | " | 150 |  | 15 |  |
| 19 | Ex. 15 (coated Bialaphos) | 60 |  |  | 4.1 |
|  | Ex. 15 (coated Bialaphos) | 125 |  |  | 4.9 |
|  | Ex. 15 (coated Bialaphos) | 250 |  |  | 5.7 |
|  | Ex. 15 (coated Bialaphos) | 500 |  |  | 7.2 |
|  | Bialaphos | 60 |  |  | 0.4 |
|  | " | 125 |  |  | 0.9 |
|  | " | 250 |  |  | 1.7 |
|  | " | 500 |  |  | 2.4 |

| Test | Concn. | P.V. for G.M. of | P.V. for G.M. of |

TABLE II-continued

| No. | Formulation Tested | (ppm) | cucumber | tomato |
|---|---|---|---|---|
| 20 | Ex. 16 (coated CuSO$_4$.5H$_2$O) | 10 | 90 | 85 |
|  | Ex. 16 (coated CuSO$_4$.5H$_2$O) | 20 | 92 | 91 |
|  | Ex. 16 (coated CuSO$_4$.5H$_2$O) | 40 | 98 | 96 |
|  | Ex. 16 (coated CuSO$_4$.5H$_2$O) | 80 | 99 | 99 |
|  | GANDY W.P.[1] | 10 | 0 | 0 |
|  | " | 20 | 0 | 0 |
|  | " | 40 | 2 | 5 |
|  | " | 80 | 5 | 8 |
| 21 | Ex. 17 (coated CuSO$_4$) | 25 | 91 | 95 |
|  | Ex. 17 (coated CuSO$_4$) | 50 | 92 | 95 |
|  | Ex. 17 (coated CuSO$_4$) | 100 | 98 | 99 |
|  | CuSO$_4$ | 25 | 0 | 0 |
|  | " | 50 | 0 | 0 |
|  | " | 100 | 3 | 5 |
| 22 | Ex. 18 (coated Cu 8-oxyqunoline) | 10 | 85 | 91 |
|  | Ex. 18 (coated Cu 8-oxyqunoline) | 20 | 88 | 95 |
|  | Ex. 18 (coated Cu 8-oxyqunoline) | 40 | 92 | 97 |
|  | Ex. 18 (coated Cu 8-oxyqunoline) | 80 | 97 | 99 |
|  | Oxindo 80 W.P.[2] | 10 | 15 | 21 |
|  | " | 20 | 25 | 23 |
|  | " | 40 | 38 | 35 |
|  | " | 80 | 40 | 52 |
| 23 | Ex. 19 (coated basic copper chloride) | 50 | 88 | 87 |
|  | Ex. 19 (coated basic copper chloride) | 100 | 93 | 88 |
|  | Ex. 19 (coated basic copper chloride) | 150 | 96 | 95 |
|  | Cupravit forte W.P.[3] | 50 | 0 | 0 |
|  | " | 100 | 5 | 8 |
|  | " | 150 | 7 | 8 |
|  | Ex. 20 | 50 | 95 | 82 |
|  | " | 100 | 99 | 85 |
|  | " | 150 | 99 | 89 |
|  | " | 200 | 99 | 92 |
|  | GANDY W.P. | 50 | 0 | 5 |
|  | " | 100 | 0 | 8 |
|  | " | 150 | 7 | 15 |
| 25 | Ex. 21 | 60 | 95 | 91 |
|  | " | 125 | 94 | 94 |
|  | " | 250 | 98 | 97 |
|  | " | 500 | 99 | 99 |
|  | Oxindo 80 W.P. | 60 | 0 | 0 |
|  | " | 125 | 0 | 8 |
|  | " | 250 | 25 | 21 |
|  | " | 500 | 50 | 43 |
| 26 | Ex. 22 | 10 | 85 | 92 |
|  | " | 20 | 91 | 96 |
|  | " | 40 | 98 | 99 |
|  | " | 80 | 99 | 99 |
|  | Benlate | 10 | 0 | 0 |
|  | " | 20 | 0 | 0 |
|  | " | 40 | 2 | 0 |
|  | " | 80 | 5 | 5 |

*P.V. and G.M. mean prevention value and grey mildew, respectively.
[1] GANDY W.P., 47.5% CuSO$_4$ (Agro Kanesho Co., Ltd.).
[2] Oxindo 80 W.P., 80% Copper 8-quinolinolate (Tomono Noyaku Co., Ltd.).
[3] Cupravit forte W.P., Copper oxychloride (Cu content: 44%)

TEST EXAMPLES 27 to 39

Aqueous solutions of each of the coated agricultural formulations, agricultural formulations or agricultural chemicals having concentrations of 200 and 500 ppm were prepared and the prevention values and the phytotoxicity thereof were determined. The results are summarized in table III.

In each test Nos. 27 to 39, the coated formulations of the present invention exhibit prevention values higher than those of the foregoing agricultural formulations and simple aqueous solution of agricultural chemicals. In all the tests, the phytotoxicity of these agricultural chemicals was not observed.

TABLE III

The prevention effect of various coated carbonates, hydrogen carbonates on citrus melanose.

| Test No. | Formulation tested | Concn. (ppm) | Prevention Value (%) | Phytotoxicity |
|---|---|---|---|---|
| 27 | coated NaHCO$_3$ formulation | 500 (200) | 100(100) | none |
|  | NaHCO$_3$ formulation | 500 (200) | 70(21) | none |
|  | NaHCO$_3$ | 500 (200) | 40(3) | none |
|  | coated Na$_2$CO$_3$ formulation | 500 (200) | 98(95) | none |
|  | Na$_2$CO$_3$ formulation | 500 (200) | 65(18) | none |
|  | Na$_2$CO$_3$ | 500 (200) | 38(0) | none |
| 29 | coated K$_2$CO$_3$ formulation | 500 (200) | 100(93) | none |
|  | K$_2$CO$_3$ formulation | 500 (200) | 67(21) | none |
|  | K$_2$CO$_3$ | 500 (200) | 35(11) | none |
| 30 | coated CaCO$_3$ formulation | 500 (200) | 92(90) | none |
|  | CaCO$_3$ formulation | 500 (200) | 62(12) | none |
|  | CaCO$_3$ | 500 (200) | 30(5) | none |
| 31 | coated (NH$_4$)$_2$CO$_3$ formulation | 500 (200) | 88(80) | none |
|  | (NH$_4$)$_2$CO$_3$ formulation | 500 (200) | 57(10) | none |
|  | (NH$_4$)$_2$CO$_3$ | 500 (200) | 19(0) | none |
| 32 | coated (NH$_4$)HCO$_3$ formulation | 500 (200) | 86(80) | none |
|  | (NH$_4$)HCO$_3$ formulation | 500 (200) | 53(7) | none |
|  | (NH$_4$)HCO$_3$ | 500 (200) | 16(0) | none |
| 33 | coated NaCl formulation | 500 (200) | 92(90) | none |
|  | NaCl formulation | 500 (200) | 84(22) | none |
|  | NaCl | 500 (200) | 22(2) | none |
| 34 | coated KCl formulation | 500 (200) | 94(90) | none |
|  | KCl formulation | 500 (200) | 62(12) | none |
|  | KCl | 500 (200) | 31(0) | none |
| 35 | coated KHCO$_3$ formulation | 500 (200) | 94(90) | none |
|  | KHCO$_3$ formulation | 500 (200) | 57(23) | none |
|  | KHCO$_3$ | 500 (200) | 51(3) | none |
| 36 | coated Na$_2$HPO$_4$ formulation | 500 (200) | 87(80) | none |
|  | Na$_2$HPO$_4$ formulation | 500 (200) | 41(11) | none |
|  | Na$_2$HPO$_4$ | 500 (200) | 20(0) | none |
| 37 | coated NaH$_2$PO$_4$ formulation | 500 (200) | 86(83) | none |
|  | NaH$_2$PO$_4$ formulation | 500 (200) | 22(12) | none |
|  | NaH$_2$PO$_4$ | 500 (200) | 10(0) | none |
| 38 | coated K$_2$HPO$_4$ formulation | 500 (200) | 88(85) | none |
|  | K$_2$HPO$_4$ formulation | 500 (200) | 31(15) | none |

TABLE III-continued

The prevention effect of various coated carbonates, hydrogen carbonates on citrus melanose.

| Test No. | Formulation tested | Concn. (ppm) | Prevention Value (%) | Phytotoxicity |
|---|---|---|---|---|
| | $K_2HPO_4$ | 500 (200) | 12(5) | none |
| 39 | coated $KH_2PO_4$ formulation | 500 (200) | 87(81) | none |
| | $KH_2PO_4$ formulation | 500 (200) | 34(14) | none |
| | $KH_2PO_4$ | 500 (200) | 7(3) | none |
| Control | none | 0(0) | 0(0) | none |

Note: The prevention values given in the brackets corresponds to the data obtained when the agricultural chemicals were used at the concentration given in the brackets.

The prevention effect of the agricultural formulations on black spot disease of oranges were examined with respect to the aqueous solution of $NaHCO_3$ (Δ - - - Δ), a formulation of J. P. KOKAI No. 63-233902 (this could be prepared by suspending 80 to 200 parts of $NaHCO_3$ in 100 parts of 3/1 mixture of oleic acid monoglyceride and glycerin monooctoate; □ - - - □) and the coated $NaHCO_3$ formulation (○ - - - ○) while changing the concentration thereof and the results were plotted in FIG. 1 (Test Example 27).

When the concentration was changed between 0 and 2,000 ppm, the prevention value of the aqueous solution of conventional agricultural chemicals reaches only 10% at 2,000 ppm and the formulation of J. P. KOKAI No. 63-233902 requires about 1,000 ppm to attain the prevention value of 80%. On the contrary, the prevention value of as high as 97% was attained by using the coated formulation of the invention only at 250 ppm. This clearly indicates that the coated formulation of the invention is extremely effective even at a concentration lower than that of the other two formulations.

Figure 2:
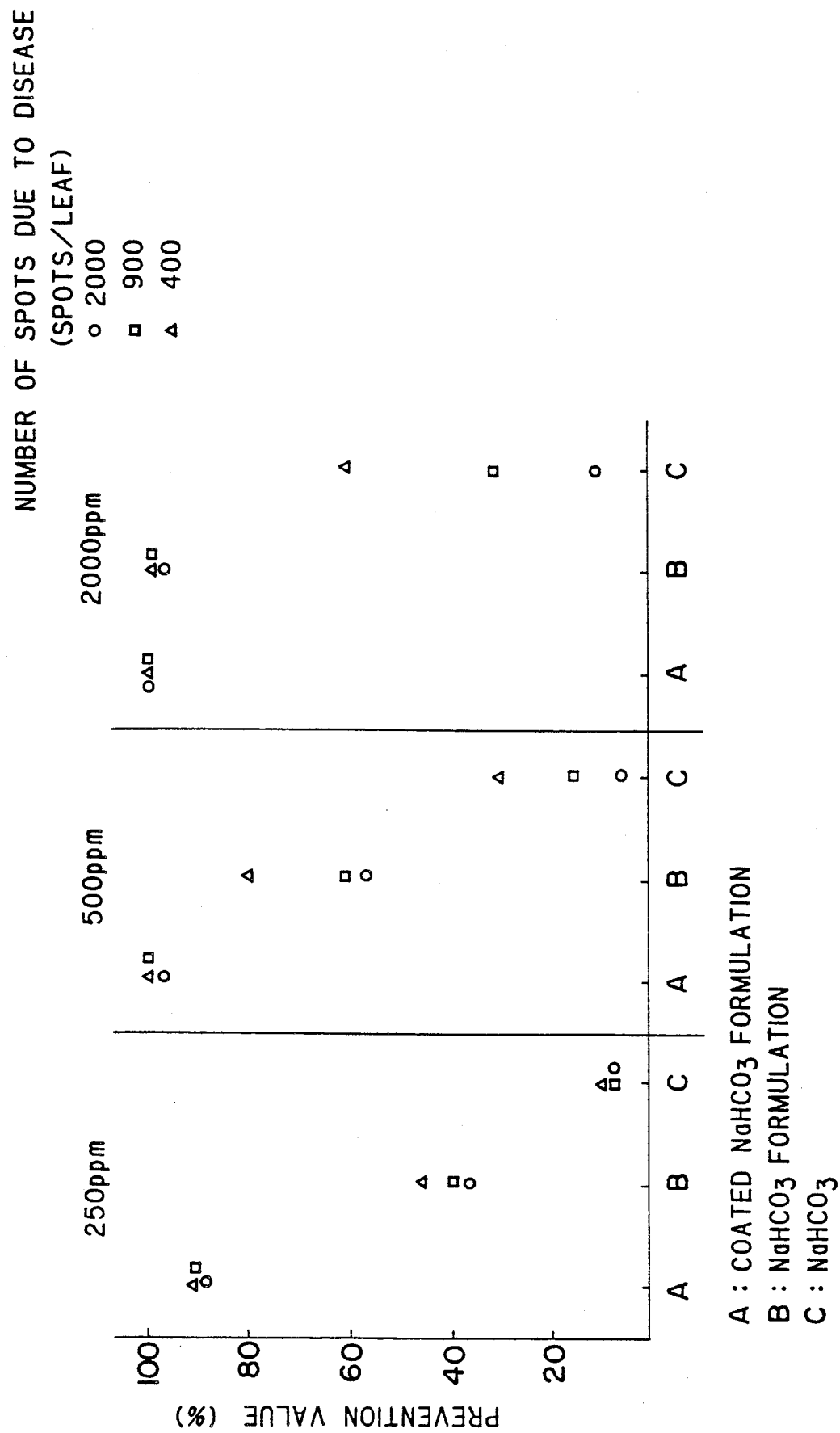
FIG. 2 shows the relation between the prevention value of various agricultural formulations and the forms thereof while taking the number of spots due to disease into consideration and changing the concentration of the formulations.

FIG. 2 is a diagram illustrating the relationship between the prevention value and three different forms of the formulation used while taking into consideration the state of occurrence of citrus melanose (number of spots due to disease: 2,000/leaf (○): 900/leaf (□) and 400/leaf (Δ)) and changing the concentration (250, 500 and 2,000 ppm). In this figure, A denotes the coated formulation of the invention, B $NaHCO_3$ formulation and C an aqueous solution of uncoated $NaHCO_3$. .PA As shown in FIG. 2, the coated formulation of the invention shows high prevention values at every concentrations examined regardless of whether the state of disease is severe and effectively suppresses the citrus melanose. On the other hand, the agricultural formulation of J. P. KOKAI No. 63-233902 (this was prepared by suspending 80 to 200 parts of $NaHCO_3$ in 100 parts of 3/1 mixture of oleic acid monoglyceride and glycerin monooctoate) and an aqueous solution of the uncoated $NaHCO_3$ are effective only at a relatively low number of spots due to disease even when they are used in a high concentration. In other word, they can be effective only at the initial state of the disease.

Figure 3:
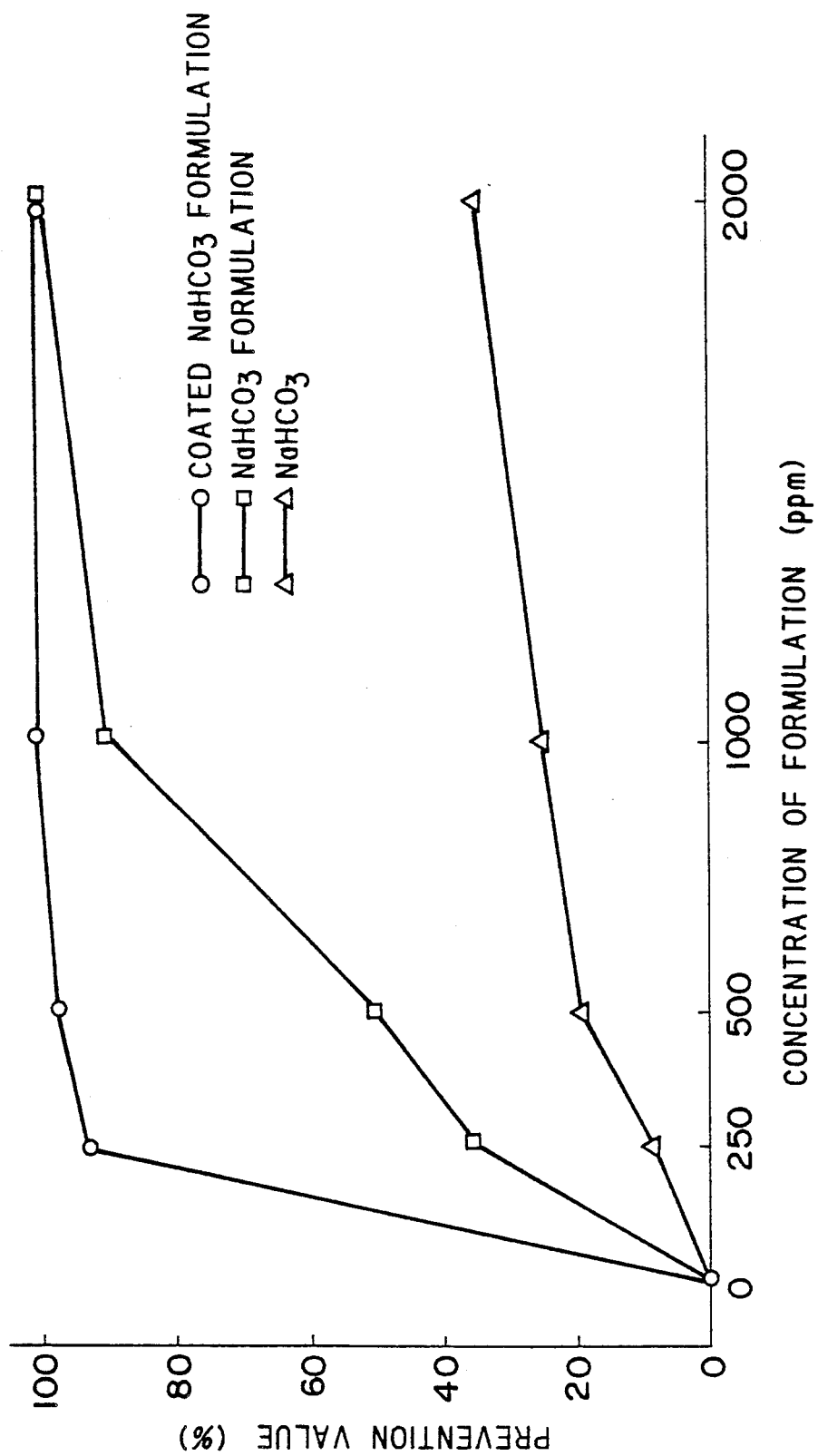
FIG. 3 shows the relation between the prevention value of various formulations with respect to mildew of cucumber and the concentration thereof, observed when the state of disease is medium (the number of spots due to disease: 200/leaf)

FIG. 3 shows the prevention values of each agricultural formulations at each concentration with respect to mildew of cucumber when the state of the disease is medium (200/leaf). In this figure, ○ - - - ○, □ - - - □ and Δ - - - Δ represent the coated $NaHCO_3$ formulation, $NaHCO_3$ formulation and aqueous solution of $NaHCO_3$ respectively (Test Example 1).

As seen from the results shown in FIG. 3, the coated agricultural formulation of the present invention shows effects superior to those observed on the other agricultural chemicals.

Figure 4:
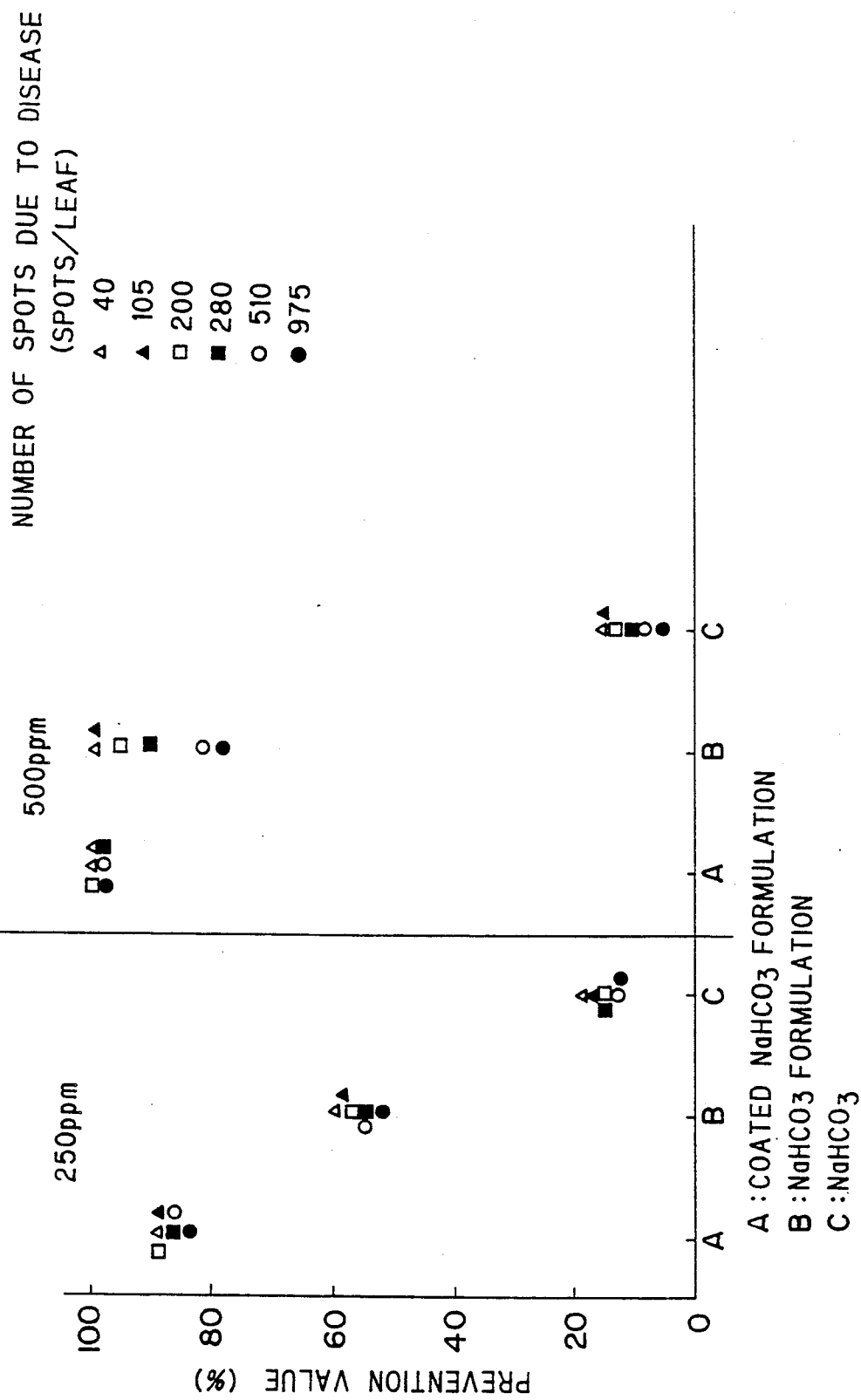
FIG. 4 shows the relation between the prevention value of various agricultural formulations for mildew of cucumber and the forms thereof while taking the state of teh disease into consideration.

FIG. 4 is a diagram illustrating the relationship between the prevention value and three different forms of the $NaHCO_3$ formulation used while taking the state of generation of mildew of cumcumber into consideration and changing the concentration as in FIG. 2.

The coated formulation of the invention can effectively suppress the mildew of cucumber in severe state at each concentration examined (250, 500 and 1,000 ppm) and is found to be a preferred agricultural chemical. In this figure, Δ, ▲, □, ■, ○, ● represent data corresponding to the number of spots due to disease of 40, 105, 200, 280, 510 and 975/leaf respectively. In addition, A, B and C are the same as those defined in FIG. 2.

Figure 5:
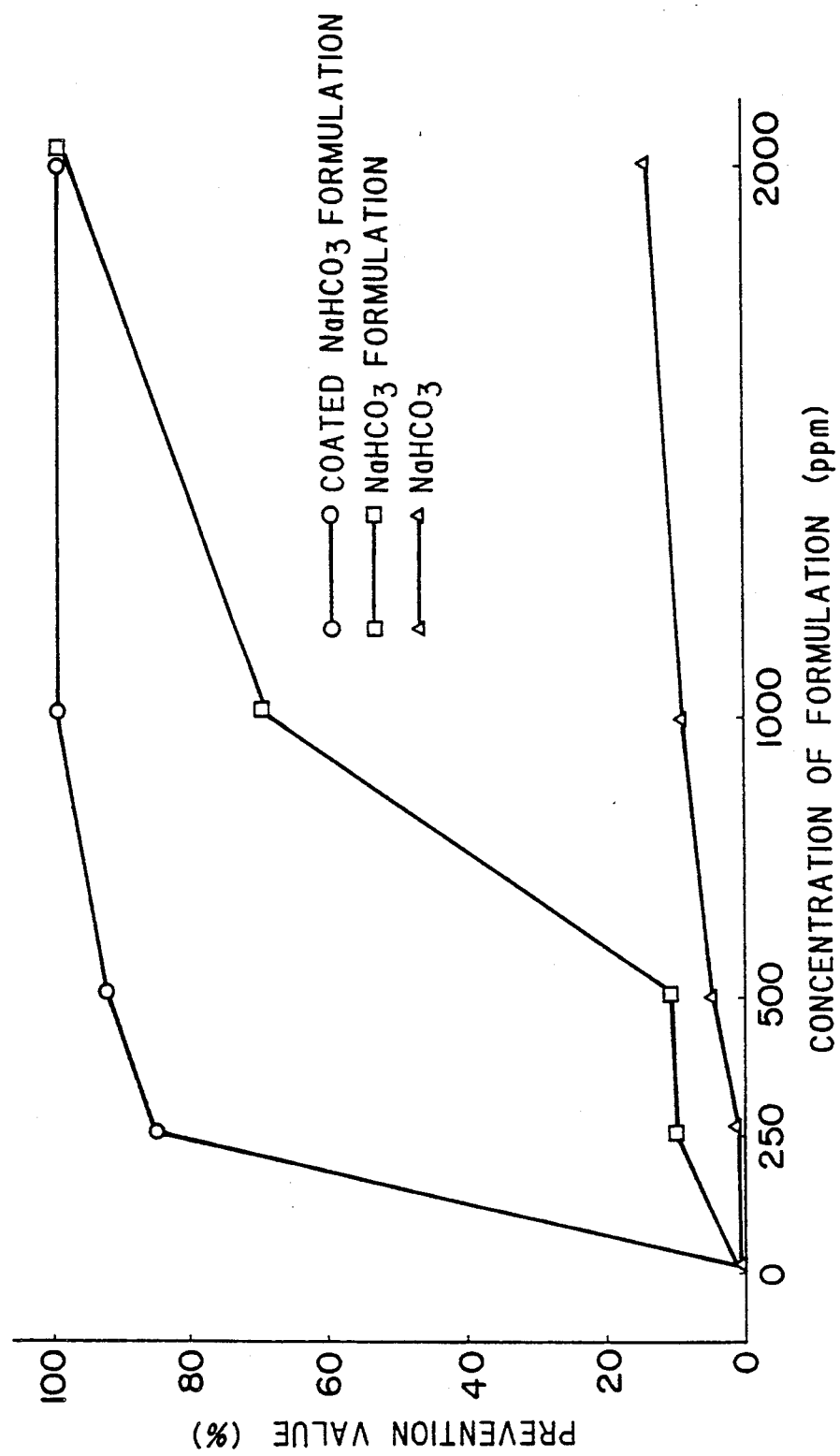
FIG. 5 shows the relation between the prevention value of various agricultural formulations and the concentration thereof observed when the state of disease is severe.

FIG. 5 is a diagram illustrating the relationship between the prevention value of $NaHCO_3$ formulations and the forms thereof used with respect to mildew of cucumber in severe sate (the number of spots due to the disease: 450/leaf) while changing the concentration of the formulations. It is found that the coated formulation of the invention can effectively suppress the mildew of cucumber in severe state compared with aqueous solution and agricultural formulation of J. P. KOKAI NO. 63-233902.

Figure 6:
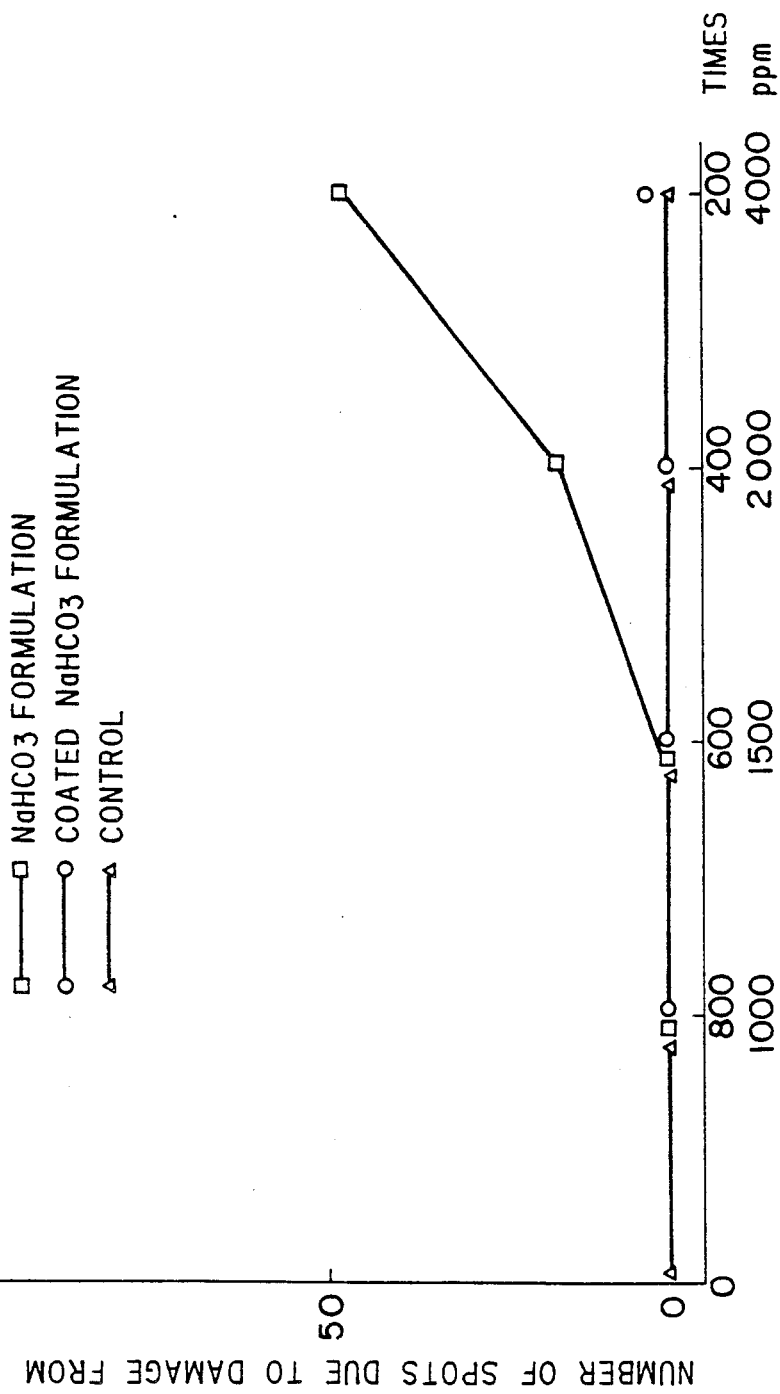
FIG. 6 is attached hereto to demonstrate the degree of phytotoxicity of the coated $NaHCO_6$ formulation, $NaHCO_3$ formulation and an aqueous solution of non-coated $NaHCO_3$ and shows the relation between the number of spots due to agricultural chemicals (phytotoxicity) and the concentration thereof observed when these are applied to cucumber.

FIG. 6 shows the relation between the concentration of each agricultural formulation and the number of spots (phytotoxicity).

It is noted that unlike the conventional aqueous solution, the agricultural formualtion of J. P. KOKAI No. 63-233902 and the coated formulation of the invention do not show phytotoxicity at a concentration fo not more than 4,000 ppm.

As discussed above in detail, the coated agricultural formulation of the present invention exhibits the prevention value superior to those of the uncoated agricultural chemicals and the aforesaid agricultural formulations (J. P. KOKAI No. 63-233902).

If using an aqueous solution of conventional agricultural chemicals and the foregoing agricultural formulation, the number of spots due to disease in general increases and the prevention value thereof is lowered as the disease proceeds while the coated agricultural formulation of the invention does not show such tendency and shows stable efficiency.

The phytotoxicity of the coated formulation of the invention, which is estimated on the basis of the number of spots due to disease, is almost the same as the observed on the control (free from agricultural chemicals).

What is claimed is:

1. A coated agricultural chemical comprising a powdery effective component of an agricultural chemical coated with at least one member selected from the group consisting of aliphatic acid esters of aliphatic polyols and phospholipids in an amount of 0.1 to 3 parts by weight per 100 parts by weight of the effective component, wherein the particle size of the effective component is adjusted so that it passes through a sieve of 100 to 400 mesh.

2. A coated agricultural chemical of claim 1 wherein it further comprises spreading agents, wetting and spreading agents and/or anchorages.

3. A coated agricultural chemical of claim 1 wherein the aliphatac polyol moieties of the esters are selected from the group consisting of saturated and unsaturated aliphatac polyols having 3 to 6 carbon atoms and the alphatic acid moieties of the esters are selected from the group consisting of saturated and unsaturated acids and mixture thereof.

4. A coated agricultural chemical of claim 3 wherein the aliphatic polyol moiety is glycerin, propylene glycol, sorbitol or sorbitan and the aliphatic acid moiety is selected from the group consisting of caprylic acid, capric acid, lauric acid, myristic acid, palmitic acid, stearic acid, arachic acid, behenic acid, oleic acid, linolic acid, linolenic acid, ricinoleic acid, tallow, cottonseed oil, rapeseed oil and hardened oil.

5. A coated agricultural chemical of claim 1 wherein the ester is selected from the group consisting of sorbitan monolaurate, sorbitan monostearate, glycerin monooleate, glycerin monooctoate, glycerin mono-soyabeen oil fatty acid ester, glycerin mono-cottonseed oil fatty acid ester and polyglycerin fatty acid esters.

6. A coated agricultural chemical of claim 1 wherein the phospholipid is selected from the group consisting of phytolecithin derived from plant's oil, egg yolk; and phosphatidylcholine, phosphatidylethanolamine and phosphatidylinositol separated therefrom.

7. A coated agricultural chemical of claim 1 the effective component is in the form of solid powder at ordinary temperature.

8. A coated agricultural chemical of claim 7 wherein the effective component is water-soluble.

9. A coated agricultural chemical of claim 7 wherein the effective component is a member selected from the group consisting of copper 8-oxyquinoline, copper sulfate, basic copper sulfate, basic copper chloride, copper(II) chloride, basic copper carbonate, methyl 1-(butylcarbamoyl)-2-benzimidazolecarbamate, antibiotic-polyoxin complex, o,o-diethyl-s-benzylthiophosphate, 2-sec-butylphenyl-N-methylcarbamate and o,o-dimethyl-2,2,2-trichloro-1-hydroxyethylphosphate; and sodium hydrogen carbonate, sodium carbonate, potassium hydrogen carbonate, potassium carbonate, calcium carbonate, ammonium carbonate, ammonium hydrogen carbonate, sodium chloride, potassium chloride, disodium hydrogen phosphate, sodium dihydrogen phosphate, dipotassium hydrogen phosphate and potassium dihydrogen phosphate.

* * * * *